US00PP22473P2

(12) United States Plant Patent
Brotzman

(10) Patent No.: US PP22,473 P2
(45) Date of Patent: Jan. 31, 2012

(54) ***WEIGELA* PLANT NAMED 'WF-2009'**

(50) Latin Name: *Weigela×hybrida*
Varietal Denomination: WF-2009

(76) Inventor: Timothy Charles Brotzman, Madison, OH (US)

( * ) Notice: Subject to any disclaimer, the term of this patent is extended or adjusted under 35 U.S.C. 154(b) by 0 days.

(21) Appl. No.: 12/927,783

(22) Filed: Nov. 22, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner* — Kent L Bell

(57) ABSTRACT

A new and distinct cultivar of *WEIGELA* plant named 'WF-2009' whose variegated foliage is mid-green in color with cream-yellow margins which occupy from 25% to 30% of leaf surface area. 'WF-2009' exhibits an upright vase-shaped habit; bears white to pale pink flowers in the spring and achieves 6 feet in height and 6 feet in width at maturity. 'WF-2009' is hardy in USDA Zone 6A and has not been observed to burn in summer in Madison, Ohio. In combination these traits set 'WF-2009' apart from all other existing varieties of *WEIGELA* known to the inventor.

2 Drawing Sheets

Genus: *WEIGELA*.
Species:×*hybrida*.
Denomination: 'WF-2009'.

BACKGROUND OF THE INVENTION

The present invention relates to a new and distinct cultivar of *WEIGELA* which is grown as an ornamental deciduous shrub for use in the garden and landscape. The new cultivar from the family Caprifoliaceae is known botanically as *WEIGELA×hybrida* and will be referred to hereinafter by the cultivar name 'WF-2009'.

'WF-2009' was first observed by the inventor in 2003 in Madison, Ohio as a naturally occurring branch sport which was growing on one plant within the inventor's commercial crop of *Weigela* 'Variegata' (unpatented). The inventor was attracted to the unusually broad yellow marginal band in the leaf. Plants propagated from the initial branch sport were observed over time and found to possess other desirable characteristics, especially a strong upright habit and an ability to withstand full sun, without scorching, during summer in Ohio.

The parent of 'WF-2009' is an individual plant of *WEIGELA* 'Variegata' which is also the closest comparison variety known to the inventor. Whereas the cream-white margins of *WEIGELA* 'Variegata' occupy a variable proportion of leaf area, typically between 5% and 10%, the cream-yellow margins of 'WF-2009' occupy between 25% and 30% of a typical leaf surface area.

'WF-2009' may also be compared with two other varieties of *Weigela* with variegated foliage, *Weigela* 'WALWEIGEYE' (U.S. Plant Pat. No. 20,842) which arose as a variegated sport of *Weigela* 'Rubidor' (unpatented) and *Weigela* 'BRIGELA' (U.S. Plant Pat. No. 12,666) which arose as a variegated sport of *Weigela* 'Bristol Ruby' (unpatented). Whereas, the flowers of both 'WALWEIGEYE' and 'Brigela' are dark red, the flowers of 'WF-2009' are white to pale pink in color. Whereas the variegation of 'WALWEIGEYE' occupies approximately 50% of leaf area and is golden yellow, the variegation of 'WF-2009' occupies approximately 25% to 30% of the leaf surface and is cream-yellow 'WF-2009' was first asexually propagated by the inventor in summer 2003 in Madison, Ohio. Asexual propagation was accomplished using softwood cuttings. Since that time, under careful observation, the distinguishing characteristics of 'WF-2009' have been determined stable and uniform, and to reproduce true to type in successive generations of asexual propagation.

SUMMARY OF THE INVENTION

The distinguishing characteristics of 'WF-2009' are as follows: In combination these traits set 'WF-2009' apart from all other existing varieties of *WEIGELA* known to the inventor. 'WF-2009' has not been tested under all possible conditions and phenotypic differences may be observed with variations in environmental, climatic, and cultural conditions.

1. 'WF-2009' exhibits lustrous variegated foliage.
2. The leaves of 'WF-2009' are mid-green with cream-yellow margins
3. The cream-yellow margins extend around the entire leaf, including the base and apex.
4. The cream-yellow margins occupy from 25% to 30% of a typical leaf surface area.
5. The new growth of the stems of 'WF-2009' is green, and ripens to red-brown.
6. 'WF-2009' achieves 60 cm. in height and 45 cm. in width after one year of growth.
7. 'WF-2009' achieves 2 meters in height and 2 meters in width at maturity.
8. 'WF-2009' exhibits white to pale pink flowers during spring.
9. 'WF-2009' exhibits upright vase-shaped habit.
10. 'WF-2009' is hardy at least in USDA Zone 6A.
11. The foliage of 'WF'-2009 has not been observed to burn in summer in Madison, Ohio.

BRIEF DESCRIPTION OF THE DRAWINGS

The accompanying color drawings illustrate the overall appearance of 'WF-2009' showing the colors of its foliage and flowers as true as it is reasonably possible to obtain of this type.

The drawing labeled

Figure 1:
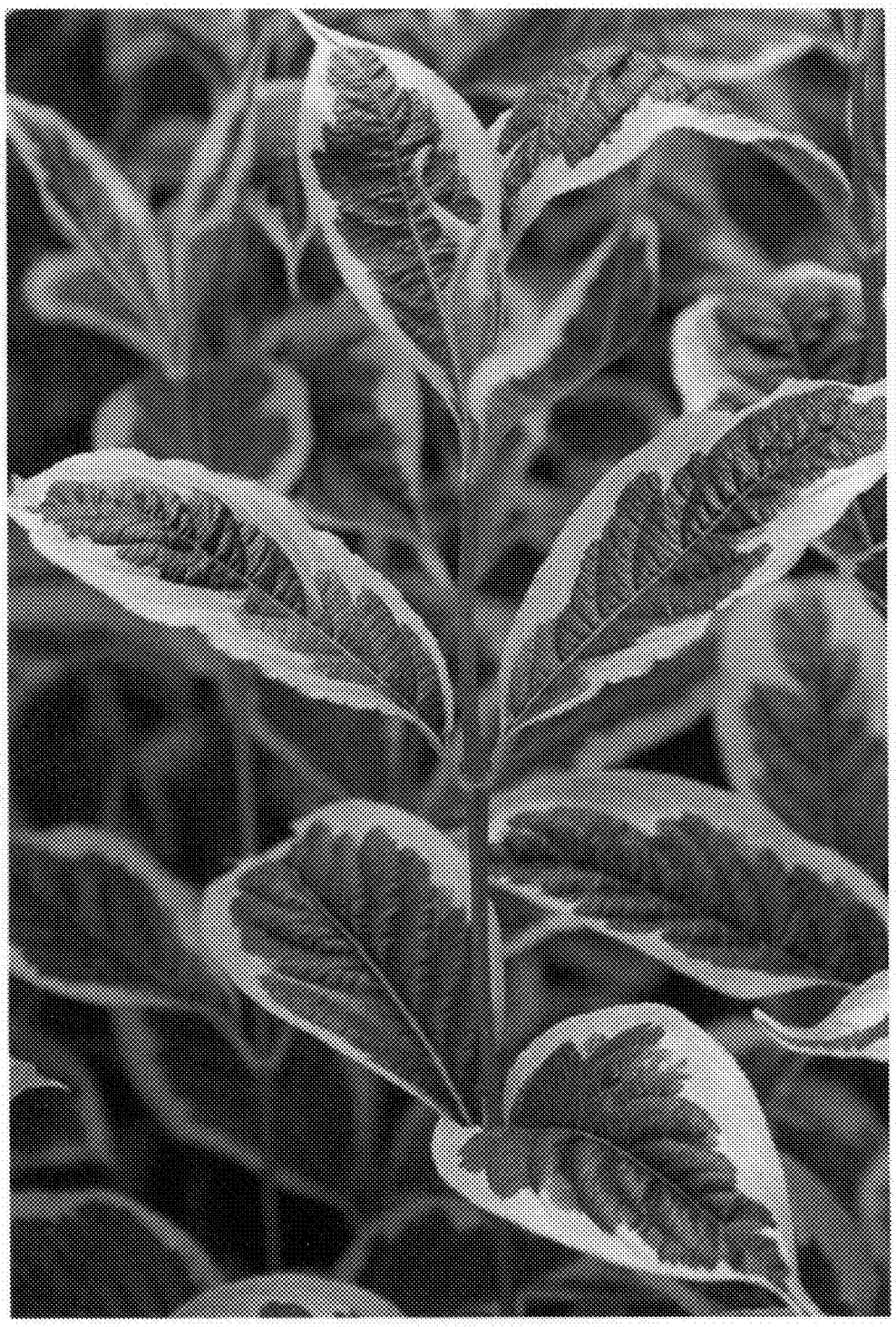
FIG. 1 presents a single stem of 'WF-2009' from a two year old plant of 'WF-2009' which has been grown out of doors in Madison, Ohio. The drawing depicts the typical variegation of the foliage of 'WF-2009'.
Figure 2:
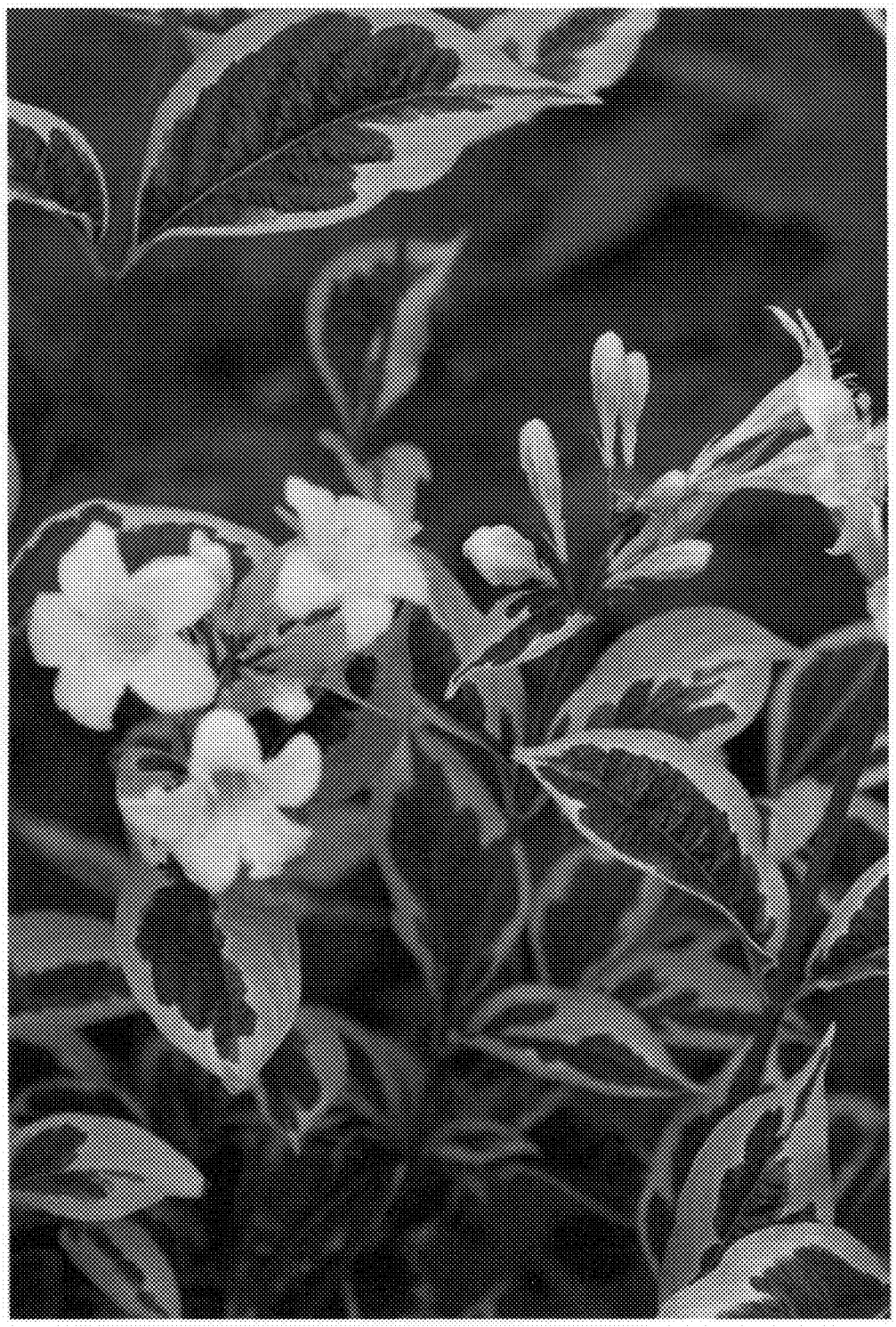

The drawing labeled as FIG. 2 presents a view of the flowers of 'WF-2009'.

BOTANICAL DESCRIPTION OF THE PLANT

The following is a detailed botanical description of the new *WEIGELA* cultivar named 'WF-2009'. Observations, measurements, values and comparisons were collected in Santa Barbara, Calif. from a one year old plant which is growing outside in medium loamy soil. Color determinations are made in accordance with The Royal Horticultural Society Colour Chart of 2007 from London England, except where general color terms of ordinary dictionary significance are used. The growing requirements of the new variety are similar to the species.

Botanical classification: *WEIGELA*×*hybrida* 'WF-2009'.
Family: Caprifoliaceae.
Genus: *WEIGELA*.
Species: ×*hybrida*.
Denomination: 'WF-2009'.
Common name: *WEIGELA*.
Parentage: *WEIGELA*×*hybrida* 'WF-2009' was discovered as a naturally occurring branch sport on an individual plant of *WEIGELA* 'Variegata'.
Propagation method: Softwood cuttings.
Rooting habit: Fibrous.
Time to develop roots (range): Approximately 30-45 days are required to develop roots from an initial cutting.
Crop time (average): 6 months are required to achieve a finished 1-liter container from a rooted cutting.
Plant habit: Upright vase-shaped.
Commercial classification: Ornamental shrub.
Use: For garden and landscape as a screen, border, or background plant.
Vigor: Moderate.
Plant dimensions (12 months): 60 cm. in height and 45 cm. in width.
Plant dimensions (at maturity, 3 years): 2 meters in height and 2 meters in width.
Hardiness: Survives at least in USDA Zone 6A.
Cultural requirements: Full sun to partial shade, regular water, and well-draining soil.
Pest and disease resistance or susceptibility: None known to the inventor.
Basal branches:
- *Number.*—8-10.
- *Stem color.*—177A (mature); 179A (semi-mature); 146C (soft growth, towards apex).
- *Stem shape.*—Cylindrical.
- *Stem diameter.*—7 mm at soil level; 3 mm towards apex.
- *Stem length* (*maximum*).—60 cm.
- *Internode* (*range*).—3 cm. to 6 cm.
- *Stem surface.*—Scurfy.

Lateral branches (plant unpinched):
- *Number.*—0-3 per basal stem from lower nodes.
- *Stem color.*—146C.
- *Stem shape.*—Cylindrical.
- *Stem diameter.*—3-5 mm.
- *Stem length.*—Up to 20 cm.
- *Stem surface.*—Scurfy.

Foliage:
- *Type.*—Winter deciduous.
- *Leaf arrangement.*—Opposite.
- *Leaf division.*—Simple.
- *Leaf shape.*—Oval.
- *Leaf length* (*average*).—7.5 cm.
- *Leaf width* (*average*).—3.5 cm.
- *Leaf apex.*—Acuminate.
- *Leaf base.*—Cuneate.
- *Leaf color* (*cream-yellow margin, adaxial surface*).—Predominantly 3B, becoming 3C then 3D towards margin.
- *Leaf color* (*cream-yellow margin abaxial surface*).—3D.
- *Leaf color* (*central green area, both surfaces.*—Ranges between and including 135A and 135B.
- *Leaf venation pattern.*—Pinnate.
- *Vein color* (*central midrib, both surfaces*).—3C.
- *Vein color* (*lateral veins*).—Indistinguishable from adjacent leaf lamina.
- *Leaf margin.*—Serrulate.
- *Leaf surface* (*adaxial*).—Puberulent.
- *Leaf surface* (*abaxial*).—Villous.
- *Leaf attachment.*—Petiolate.
- *Petiole shape.*—Cylindrical.
- *Petiole length* (*range*).—3-5 mm. in length and 1 mm. in width.
- *Petiole surface.*—Villous.
- *Petiole color.*—146C.

Flower:
- *Inflorescence type.*—Corymb, flowers borne in clusters of 4 to 10.
- *Inflorescence dimensions.*—8 cm in height, 8-12 cm in width.
- *Corolla shape.*—Funnel.
- *Corolla color* (*ventral-surface*).—62B towards base, becoming paler N155B to NN155D towards apex.
- *Corolla color* (*dorsal surface*).—62B.
- *Corolla diameter.*—2 cm.
- *Corolla depth.*—3.0 cm-3.5 cm.
- *Lobes.*—5 in number.
- *Lobe color* (*abaxial and adaxial surfaces*).—N155C to NN155D.
- *Lobe dimensions.*—8 mm in width and 10 mm. in length.
- *Fused or unfused.*—Partially fused.
- *Lobe apex.*—Rounded.
- *Lobe surface* (*abaxial and adaxial*).—Glabrous.
- *Lobe margin.*—Entire.
- *Lobe arrangement in bud.*—Imbricate.
- *Bud dimensions* (*average*).—2 cm. in length and 0.75 cm. in width.
- *Bud apex* (*range*).—Rounded.
- *Bud shape.*—Ovoid.
- *Bud color.*—62B.
- *Bud surface.*—Puberulent.
- *Flowering season.*—Late spring and early summer.
- *Lastingness of bloom* (*on the plant*).—5-7 days.
- *Aspect.*—Facing outward and upward.
- *Flower quantity* (*average, approximately*).—75-90 buds and open flowers at peak flowering.
- *Peduncle dimensions* (*average*).—5mm-8 mm in length and 2 mm. in width.
- *Peduncle shape.*—Cylindrical.
- *Peduncle surface.*—Puberulent.
- *Peduncle color.*—146C.

*Calyx shape.*—Campanulate.
*Calyx color.*—159D.
*Calyx surface.*—Villous.
*Calyx dimensions.*—4 mm in length, 3 mm in width.
*Number of sepals.*—5 in number.
*Fused or unfused.*—Unfused.
*Sepal shape.*—Lanceolate.
*Sepal apex.*—Acute.
*Sepal base.*—Cuneate.
*Sepal margins.*—Entire.
*Sepal color* (*adaxial and abaxial surfaces*).—N155C.
*Flower fragrance.*—None observed.

Reproductive organs:

*Stamens.*—5 in number.
*Stamen length* (*average*).—2.5 cm, exserted by 3-5 mm.
*Stamen color.*—159D.
*Anther length* (*average*).—3 mm.
*Anther color.*—161A.
*Pollen color.*—162A.
*Pollen quantity.*—Moderate.
*Pistil.*—1 in number.
*Pistil length* (*average*).—3 cm.
*Pistil color.*—11D.
*Stigma color.*—155A.
*Stigma length.*—<1 mm. in height; 3 mm. in width.
*Style.*—Unbranched.
*Ovary position.*—Inferior.
*Ovary shape.*—Ovoid.
*Ovary dimensions.*—3 mm. in height and 2 mm. in diameter.
*Ovary color.*—151A.

Seed: No seed has been observed to date.

The invention claimed is:

1. A new and distinct variety of *WEIGELA* plant named 'WF-2009' as illustrated and described herein.

* * * * *